US00PP07828P

United States Patent [19]

Zaiger et al.

[11] Patent Number: Plant 7,828

[45] Date of Patent: Mar. 17, 1992

[54] NECTARINE TREE "RED GLO"

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 4005 California Ave., all of Modesto, Calif. 95351

[21] Appl. No.: 619,016

[22] Filed: Nov. 28, 1990

[51] Int. Cl.[5] ..... A01H 5/00

[52] U.S. Cl. ..... Plt./41

[58] Field of Search ..... Plt./41

*Primary Examiner*—James R. Feyrer

[57] ABSTRACT

A new and distinct variety of nectarine tree with the unique combination of desirable features:

1. Early maturity of large size fruit.
2. Low winter chilling requirement of approximately 250 hours.
3. Fruit with firm flesh providing good handling and shipping quality.
4. Fruit with an attractive red skin color.
5. Heavy and regular production.
6. Ability to grow and produce in southern areas with warm winter climatic conditions, such as Indio, Calif.
7. Fruit with good flavor and eating quality.

1 Drawing Sheet

ORIGIN OF THE VARIETY

The new and distinct variety of nectarine tree originated in our experimental orchard located near Modesto, Calif. from a cross between two selected seedlings. The female parent was a peach with the identification number of 37G870 and originated from a cross between Ruby Gold Nectarine (U.S. Plant Pat. No. 3,101) and a low chilling peach of unknown origin. The pollen parent was a nectarine which originated from a cross between the low chilling nectarine Sun Red (non-patented) and the nectarine June Glo (U.S. Plant Pat. No. 5,228). The seeds were collected and grown in our experimental orchard under close observation and one low chilling seedling exhibited especially desirable early maturing fruit and was selected for asexual reproduction and commercialization.

ASEXUAL REPRODUCTION OF THE VARIETY

The new and distinct nectarine variety, asexually propagated by budding, as performed by us in our experimental orchard located near Modesto, Calif., shows that said characteristics run true to form and are established and transmitted through succeeding propagations.

SUMMARY OF THE VARIETY

The present new and distinct variety of nectarine tree is of large size, vigorous upright growth and a productive and regular bearer of large, firm, yellow flesh, clingstone fruit with good flavor and eating quality. The fruit is further characterized by having a high degree of attractive red skin color and having good storage and shipping quality. In comparison to the low chilling paternal parent, Sun Red Nectarine (non-patented), the new variety has firmer flesh, a higher degree of attractive red skin color and matures approximately one month earlier. In comparison to June Glo Nectarine (U.S. Plant Pat. No. 5,228), the new variety is lower in winter chilling requirement by approximately 600 hours and will grow and produce in the more southern fruit growing areas such as the Coachella Valley of California.

PHOTOGRAPH OF THE VARIETY

The accompanying photographs show typical specimens of the foliage and fruit of the new nectarine variety, with the upper and lower surface of the leaves being illustrated, the exterior and a fruit divided in its suture plane to reveal flesh, stone cavity and stone coloration. The photographs were taken shortly after being picked (firm ripe) and the colors are as nearly true as is reasonably possible in a color photograph of this type.

DESCRIPTION OF THE VARIETY

The following is a detailed botanical description of the new and distinct variety of nectarine tree, its flowers, foliage and fruit as based on observation of specimens grown near Modesto, Calif. with color terminology (except those in common terms) in accordance with Reinhold Color Atlas by A. Kornerup and J. H. Wanscher.

Tree:
- *Size.*—Large.
- *Vigor.*—Vigorous.
- *Form.*—Upright. Usually pruned to vase shape.
- *Production.*—Productive.
- *Bearing.*—Regular.
- *Density.*—Medium dense.

Trunk:
- *Size.*—Medium to stocky.
- *Texture.*—Shaggy to rough.
- *Color.*—Grayish brown to coffee brown (5-E-6) to (5-F-7).

Branches:
- *Size.*—Medium.
- *Texture.*—Smooth to medium rough; varies with maturity.
- *Lenticels.*—Medium number. Large size.
- *Color.*—Light brown to brown (5-D-4) to (5-D-6).

Leaves:
- *Size.*—Medium — slightly variable. Average length — 5½". Average width — 1¼".
- *Texture.*—Smooth.

*Petiole.*—Medium length. Medium thickness. Grooved in upper surface.

*Glands.*—Reniform. Number varies from 1 to 3. Average number 2. Mainly located on base of leaf blade, occasionally found on upper portion of petiole.

*Form.*—Lanceolate. Pointed.

*Margin.*—Crenate.

*Color.*—Upper surface — green to dark green (28-F-5) to (28-F-8). Lower surface — grayish green to green (28-E-6) to (28-E-7).

Flower buds:

*Size.*—Medium to large.

*Form.*—Conical, plump.

*Length.*—Medium.

*Pubescence.*—Pubescent.

Flowers:

*Blooming period.*—Early — Feb. 10, 1990 to Feb. 26, 1990. Varies slightly with climatic conditions.

*Size.*—Large — showy.

*Pollen.*—Present — self fertile.

*Color.*—Pink.

Fruit:

*Maturity when described.*—Firm ripe.

*Date of first picking.*—May 29, 1990.

*Date of last picking.*—June 6, 1990.

*Size.*—Large — comparatively uniform. Average size axially — $2\frac{3}{4}''$. Average transversely in suture plane — $2\frac{3}{4}''$.

*Form.*—Globose — nearly symmetrical, only slightly flattened at stem end.

*Suture.*—Shallow but pronounced, extends from base to apex.

*Ventral surface.*—Nearly rounded, only slightly lipped.

*Cavity.*—Rounded to slightly elongated in suture plane. Average depth — 7/16". Average breadth — $\frac{3}{4}''$.

*Apex.*—Slightly retuse on majority of fruit; varies from slight point to slight depression.

*Base.*—Retuse.

Skin:

*Thickness.*—Medium.

*Texture.*—Medium tough-tenacious to the flesh.

*Tendency to crack.*—None.

*Down.*—Wanting.

*Color.*—Dark yellow to light orange ground color (4-A-8) to (5-A-8), overspread with red (9-B-8) to (9-C-8).

Flesh:

*Texture.*—Firm, meaty.

*Amygdalin.*—Undetected.

*Juice.*—Moderate.

*Ripens.*—Even.

*Flavor.*—Good. A desirable balance between sugar and acid.

*Aroma.*—Slight.

*Eating quality.*—Good.

*Fibers.*—Small and tender.

*Color.*—Light yellow to yellow (4-A-5) to (4-A-7).

Stone:

*Type.*—Clingstone.

*Size.*—Large. Average length — $1\frac{3}{8}''$. Average width—$1\frac{1}{8}''$. Average thickness — $\frac{7}{8}''$.

*Form.*—Ovoid.

*Base.*—Usually rounded — varies from rounded to straight.

*Apex.*—Usually rounded, with only a slight pistil point on some stones.

*Sides.*—Equal to unequal.

*Surface.*—Pitted throughout, heavier toward base. Irregularly furrowed toward apex. Ridges usually rounded.

*Tendency to split.*—Very slight.

*Color.*—Light brown to brown (6-C-7) to (6-D-7).

Use:

*Market.*—local and long distance. Dessert.

Keeping quality: Good.

Shipping quality: Good.

The new and distinct nectarine tree, its flowers, foliage and fruit herein described may vary in slight detail due to climatic, soil and ecological conditions under which the variety may be grown. The botanical description is that of the new variety grown under the conditions prevailing at Modesto, Calif.

The following is claimed:

1. A new and distinct variety of nectarine tree substantially as illustrated and described; characterized by its large size, vigorous upright growth and being a regular and productive bearer of early maturing, large, firm, yellow flesh, clingstone fruit with good flavor and eating quality; the fruit is further characterized in comparison to its low chilling paternal parent Sun Red Nectarine (non-patented), by having firmer flesh, a higher degree of attractive red skin color and ripening one month earlier, and in comparison to June Glo Nectarine (U.S. Plant Pat. No. 5,228), the new variety is lower in chilling by approximately 600 hours and will grow and produce in more southern fruit growing areas.

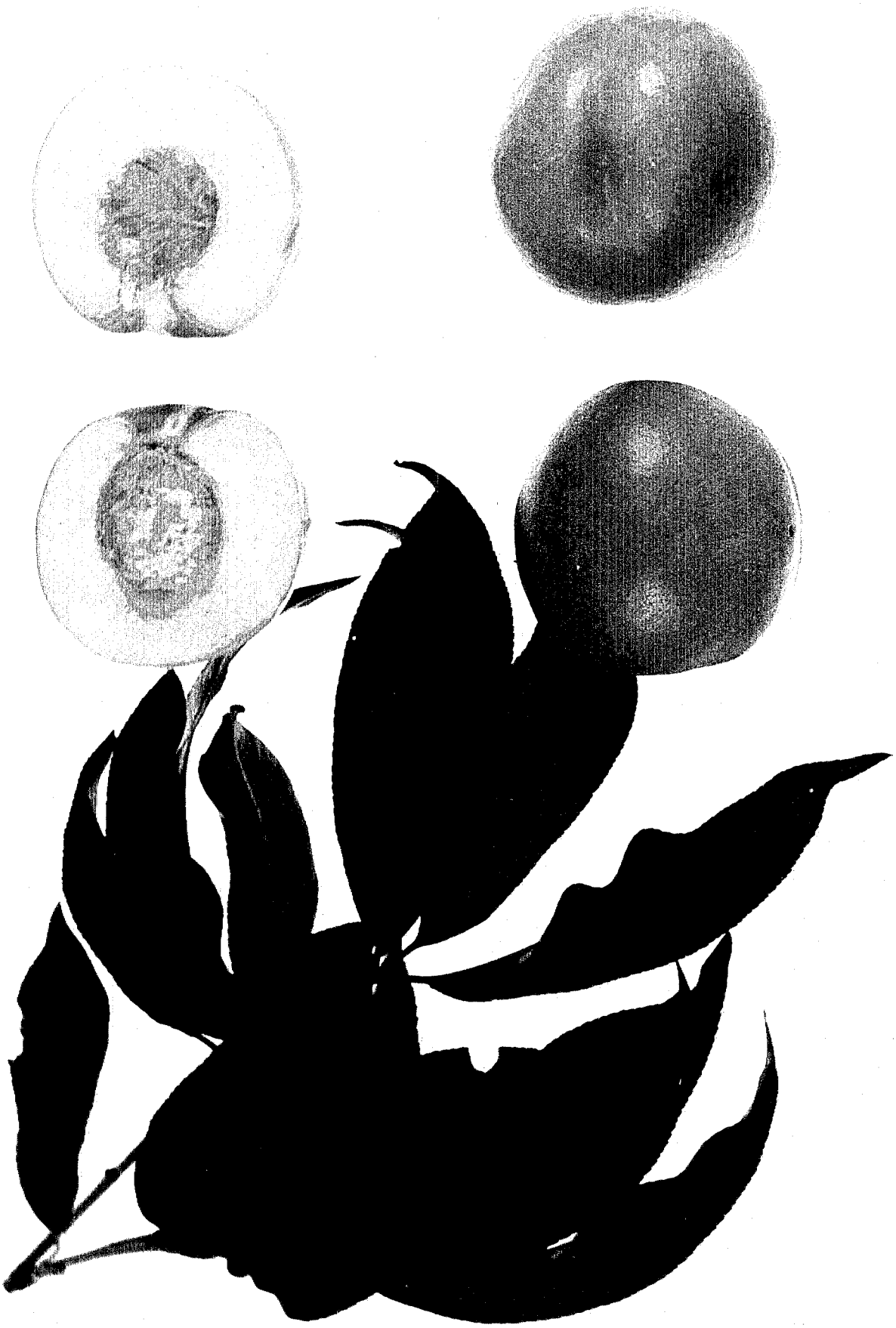

* * * * *